(12) United States Patent
Singh et al.

(10) Patent No.: US 10,540,478 B2
(45) Date of Patent: Jan. 21, 2020

(54) COMPUTERIZED SYSTEM AND METHOD FOR IDENTIFYING MEMBERS AT HIGH RISK OF FALLS AND FRACTURES

(71) Applicant: Humana Inc., Louisville, KY (US)

(72) Inventors: Harpreet Singh, Louisville, KY (US); Vipin Gopal, Louisville, KY (US)

(73) Assignee: Humana Inc., Louisville (*) Notice: Subject to any disclaimer, the term of this patent is extended or adjusted under 35 U.S.C. 154(b) by 479 days.

(21) Appl. No.: 14/180,717

(22) Filed: Feb. 14, 2014

(65) Prior Publication Data

US 2016/0357930 A1 Dec. 8, 2016

Related U.S. Application Data

(60) Provisional application No. 61/777,095, filed on Mar. 12, 2013.

(51) Int. Cl.
*G16H 50/30* (2018.01)
*G16H 50/70* (2018.01)
*G06F 19/00* (2018.01)

(52) U.S. Cl.
CPC ............ *G06F 19/00* (2013.01); *G16H 50/30* (2018.01); *G16H 50/70* (2018.01)

(58) Field of Classification Search
None
See application file for complete search history.

(56) References Cited

U.S. PATENT DOCUMENTS

2008/0009686 A1* 1/2008 Hendrich ............... A61B 5/412
600/301
2011/0082672 A1* 4/2011 Hardigan ............ G06F 19/3437
703/2
2011/0295621 A1* 12/2011 Farooq .................. G06F 19/322
705/3
2013/0096934 A1* 4/2013 Vaccaro .............. G06F 19/3431
705/2

OTHER PUBLICATIONS

Skelton et al, What are the main risk factors for falls amongst older people and what are the most effective interventions to prevent these falls?, Mar. 2004, WHO Regional Office for Europe <http://www.euro.who.int/_data/assets/pdf_file/0018/74700/E82552.pdf>.*
Mathers et al, Incidence and Characteristics of Fall-related Emergency Department Visits, Academic Emergency Medicine, vol. 5 Issue 11, pp. 1064-1070, Nov. 1998.*
Verduin et al, Temporal Abstraction for Feature Extraction: A Comparative Case Study in Prediction From Intensive Care Monitoring Data, Artificial Intelligence in Medicine, 41, 1-12 (Year: 2007).*

* cited by examiner

*Primary Examiner* — Dennis W Ruhl
*Assistant Examiner* — William G Lultschik
(74) *Attorney, Agent, or Firm* — Standley Law Group LLP

(57) ABSTRACT

A computerized system and method for automatically estimating the likelihood of having a fall leading to a fracture/dislocation within a specified period is described, and comprises a predictive model for guiding patients to the right course of treatment and encouraging discussions with their doctors for better outcomes. The system and method extracts member's health information from health administrative claims data, including clinical and pharmacy data, and estimates the probability of a fall for that member. Patients with high risk scores are selected for various clinical programs and interventions to manage their health conditions and reduce their likelihood of falling.

3 Claims, 9 Drawing Sheets

COMPUTERIZED SYSTEM AND METHOD
FOR IDENTIFYING MEMBERS AT HIGH
RISK OF FALLS AND FRACTURES

CROSS-REFERENCE TO RELATED
APPLICATIONS

This application claims priority to U.S. Provisional Patent Application Ser. No. 61/777,095, filed Mar. 12, 2013, titled COMPUTERIZED SYSTEM AND METHOD FOR IDENTIFYING MEMBERS AT HIGH RISK OF FALLS AND FRACTURES, the contents of which is incorporated herein by reference.

BACKGROUND OF THE INVENTION

Unintentional falls are one of the major health risks for adults over 65 years of age. Every year one-third of older adults, 65+ years, fall. Falls are indeed the leading cause of injury death in older adults. In 2008 alone, 19,700 people died because of injuries resulting from unintentional falls. And while some falls may only lead to moderate to severe non-life threatening injuries, the psychological effect of falls is also severe. Some studies estimated the number of unintentional falls in 2009 at 2.2 million. Five hundred eighty-one thousand of these falls resulted in hospitalization. People who have fallen once often develop a fear of falling again. This fear leads them to limit their day-to-day activities, which further leads to reduced mobility resulting in deteriorating physical fitness level. This in turn puts them at an even greater risk of falling [1].

Falls (fatal and non-fatal) can be very costly for the health care system. According to the numbers reported by CDC, falls among older adults in 2000 cost the U.S. healthcare system over $19 billion [1]. According to another study the cost of fatal fall related injuries in 2005 totaled around $349 million: $160 million for men and $189 million for women [2]. There is a direct cost related to falls which accounts for what insurance companies, patients, and health care system pays for treating fall related fracture/injuries etc., and there is an indirect cost which represents the follow-up long term cost of care. Cost of hospital care following an injurious fall among the elderly is also higher at $6.5 billion as estimated in 2006 by one study [2]. It's estimated that by 2020, the annual direct and indirect cost of fall injuries is expected to reach $54.9 billion [1].

Because falls are a high risk for patients due to diminished lifestyle, and health care payers due to monetary implications, it is in the best interest of both parties to reduce unintentional falls. However, reducing the number of falls is difficult. Unlike severe medical conditions such as cancer etc., a fall is not a single medical condition and as such, does not have a set definition. The current definition of a fall that is widely used is "unintentionally coming to rest on the ground, floor or other lower level." Falls result due to multiple medical conditions that a patient may have or medications that they may be taking. Most of the current efforts directed toward reducing falls consist of questionnaires given to patients at physician visits and deciding the risk of fall for patients based on these questions. Because there is no set definition of a fall, there is also no set "rule of thumb" questionnaire that could be used as a baseline for predicting the risk of falls for a patient. Multiple studies in the past have shown various medical conditions and medications that are connected to falls like fracture, injuries, difficulty walking, breathing problems, high risk medications such as benzodiazepines [3], [4].

Although the questionnaire based methods are widely used to ascertain the risk of falling for a member, there is no automated "proactive" system that could notify the health care provider or physician about the risk of falls for a person. Patients as well as health care providers and payers can all benefit from such a system because it would reduce expenditure for avoidable injuries and lead to a better lifestyle for the patient. There is a need for an automated falls prediction system and method that can identify the falls risk (probability of fall) for each patient and further direct them to the proper course of intervention.

SUMMARY OF THE INVENTION

A computerized system and method according to the present disclosure comprises a supervised predictive model in order to identify members who are at-risk of falling, and to estimate their likelihood of falling during a specified period (e.g., in the next 12 months). In an example embodiment, the automated predictive model is developed using clinical and non-clinical member-specific data to predict the probability/likelihood of a member falling within 12 months of identification at risk. Multiple medical conditions and/or medications are used as triggers to identify at-risk population. These triggers or risk factors may be used to assign members to relevant clinical programs/interventions. In an example embodiment, a computerized system and method to estimate the fall risk of a member in the next 12 months is provided. The system comprises of a set of triggers based on member's profile which may include information about a person's medical conditions, prescriptions, etc. that indicate the member may be at risk for a fall.

Members with high falls scores are selected for participation in various existing clinical programs or special intervention programs are created for them in order to help them manage their health and mitigate the risk of falling. Members may be stratified into different risk groups based on the severity of their likelihood to fall (i.e., high risk score). Different programs are then tailored in order to educate members about their health conditions and provide specific recommendations related to monitoring their gait, health status, types of medications, follow-up visits with health care providers etc. Patient compliance with intervention efforts can be monitored to identify those patients that are at high risk for falling and injuring themselves.

DETAILED DESCRIPTION

TABLE 1

| Glossary | |
|---|---|
| Triggers/Risk factors | Medical conditions based on diagnosis codes, and medications or combination of medications which are used to identify an initial set of members for model training. Not everyone is at a risk of falling so these triggers help identify people who are at some risk of falling. |
| Training Triggers | Medical conditions used for building the training population. |
| Model Triggers | Medical conditions used in the model once it has been trained. These may or may not be the same as the training triggers. |
| Predictors/Features | Variables created for model building/usage from different data sources (medical claims, pharmacy claims, demographic information, etc.). Some of the triggers can also be used as predictors so triggers could be considered a subset of predictors. |
| Top Predictors/Features | Predictors that the model identified as the most important for identifying who is at a high risk of falling. |
| Temporal Features | Variables created for model building/usage from different data sources that capture the relationship between time and medical/pharmacy conditions. |
| Risk Score | A numerical/character score generated by the model representing the likelihood of a member having a fall in the future. |
| Score Date | Date on which the model is ran in order to generate a risk score of falling. |

Figure 1:
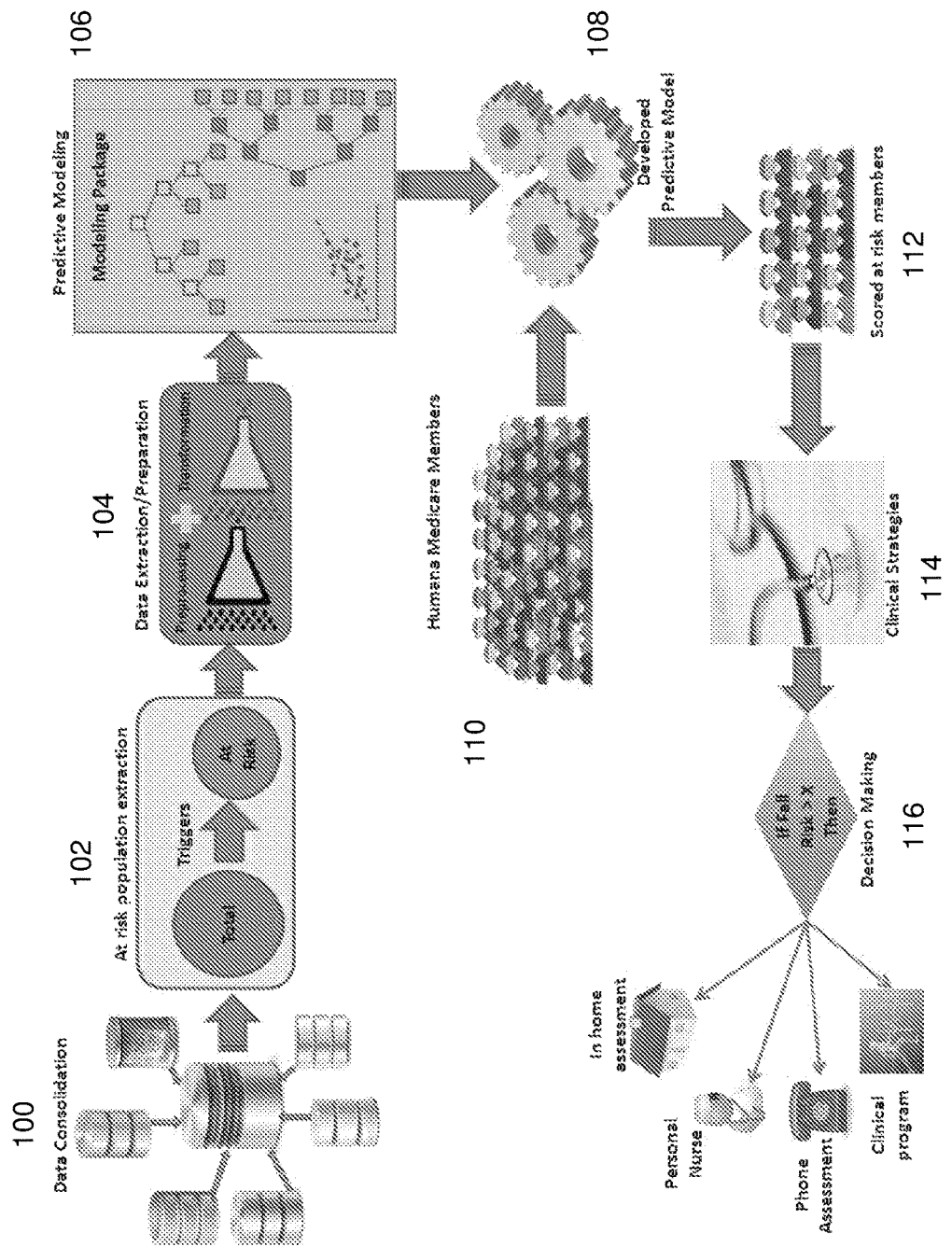
FIG. 1 is a block diagram illustrating development and application of a Falls predictive model and model application according to an example embodiment.

In an example embodiment, a predictive model for falls is integrated in a model software application for use by a health benefits provider with a covered patient-member population. The computerized system and method is helpful in identifying high risk members who will likely fall within a specified period (e.g., one year). Referring to FIG. 1, a block diagram illustrating the process of development and application of a falls predictive model according to an example embodiment is shown. Historical member data, including clinical, medical, and pharmacy claims data and consumer data such as demographic data, geographic data and financial data 100, is preprocessed and transformed using various well-known techniques 102, 104 before input to a predictive model 106. The preprocessing algorithms include variable selections, principle component analysis, and clustering and so on. A falls predictive model 108 is developed using a combination of various well-known techniques as listed in Table 2.

TABLE 2

| Predictive Model Techniques | |
|---|---|
| Modeling Technique | Description |
| Decision Tree | Tree-shaped structures that represent sets of decisions which generate rules for the classification of a dataset. |
| Logistic Regression | A statistical technique used to find the best-fitting linear relationship between a target (a categorical variable) and predictors. |

TABLE 2-continued

| Predictive Model Techniques | |
|---|---|
| Modeling Technique | Description |
| Artificial Neural Networks | Non-linear predictive models that learn through training and resemble biological neural networks in structure. |
| Ensemble | Combination of multiple models for consensus prediction with link functions. |

In an example embodiment, the model is a logistic regression model. The output of the predictive model is a risk score that indicates the likelihood of a member having a fall. The predictive model 108 is incorporated into a model application that is applied to a market-based member population 110. Members of the population that are at risk for falls 112 are selected for proactive clinical interventions 114, such as case management, emails or letters, for the right course of treatment. Members may be directed to a specific intervention 118 based on whether their fall risk exceeds a specified threshold 116. The use of the model with proactive clinical programs and interventions helps to improve outcomes for members and to reduce hospital-related costs for the health benefits provider.

With reference to FIG. 1, multiple data sources 100 are used as input for the falls predictive model, including medical information, pharmacy information, demographic information, and geographic information. The risk score of a member can be affected by various factors such as age, gender, previous falls and fractures, medications, and other clinical diagnosis. As such the risk score of a member is a culmination of multiple factors where some factors are determined to be better at prediction than others.

FIG. 1 also illustrates the data sources 100 and the elements that may contribute to the patient's fall score. Data sources for an example embodiment include membership information, demographic and geographic information, clinical and medical claims data, and pharmacy claims data. Those equipped in the art of predictive modeling would know that these data sources merely represent an example of the many that can be used for predictive modeling and in no way represent any limitations to the scope of this invention. Predictors used as inputs for the predictive model such as age, gender, race and states from member profile, clinical diagnosis, claims related to previous falls and fractures, and medications from pharmacy claims data are extracted 104 from these data sources.

The disclosed system and method may be implemented in a single computer environment or in a parallelized environment with multiple PC's/Servers performing varying tasks. This parallel environment could be located at just one physical space or it may be distributed at multiple remote locations connected via a computing media including but not limited to system bus, processing unit, connector cables etc.

Figure 2:
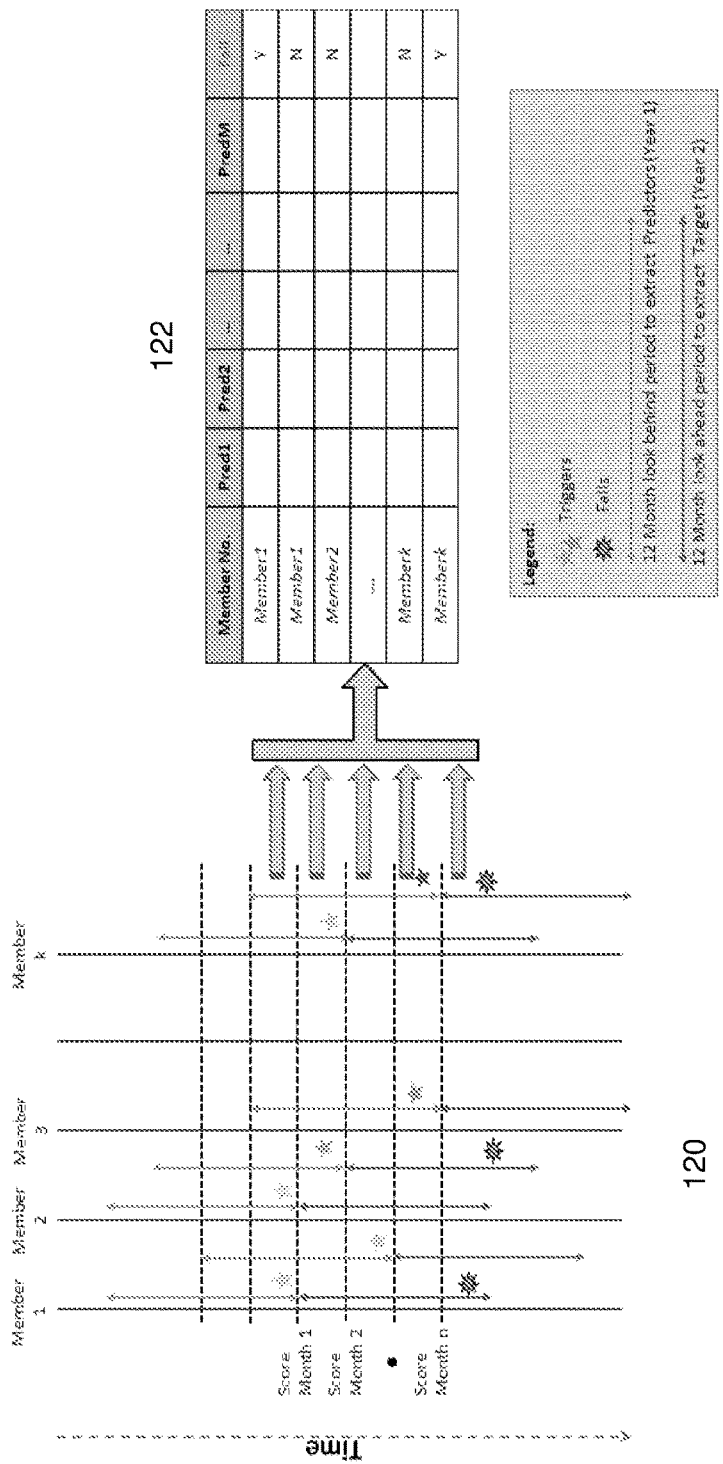
FIG. 2 is a diagram illustrating development details of a predictive model according to an example embodiment.

Referring to FIG. 2, a diagram illustrating development details of a predictive model according to an example embodiment is shown. As illustrated in FIG. 2, features extracted from one year historical membership and health administrative medical/pharmacy claims data for a covered population is used as input to a predictive modeling system 120. Using the historical member data, the model may be trained on multiple years of data thereby providing enough information to build a reliable model. In an example embodiment, medical, clinical, pharmacy, geographic, and demographic data are extracted from a centralized data server for members having at least one condition in a specified period (e.g., one month), and is then preprocessed for generating predictors as inputs of the predictive model. Each individual record represents one member with his/her statistically significant predictors. The target event, in this case falls leading to injury, is extracted from the future one year data 122. This database building process simulates a real world scenario in which the model is executed each month and the risk of falling is generated for the future 12 months. This database may be used for training/validation of the model. The 12 month restriction on historical data for predictors and future data for the target is exemplary and is not a limitation to the scope of disclosed system and method. The fall risk and predictors used to generate that risk may be extracted for N months where N is greater or less than 12.

Figure 3:
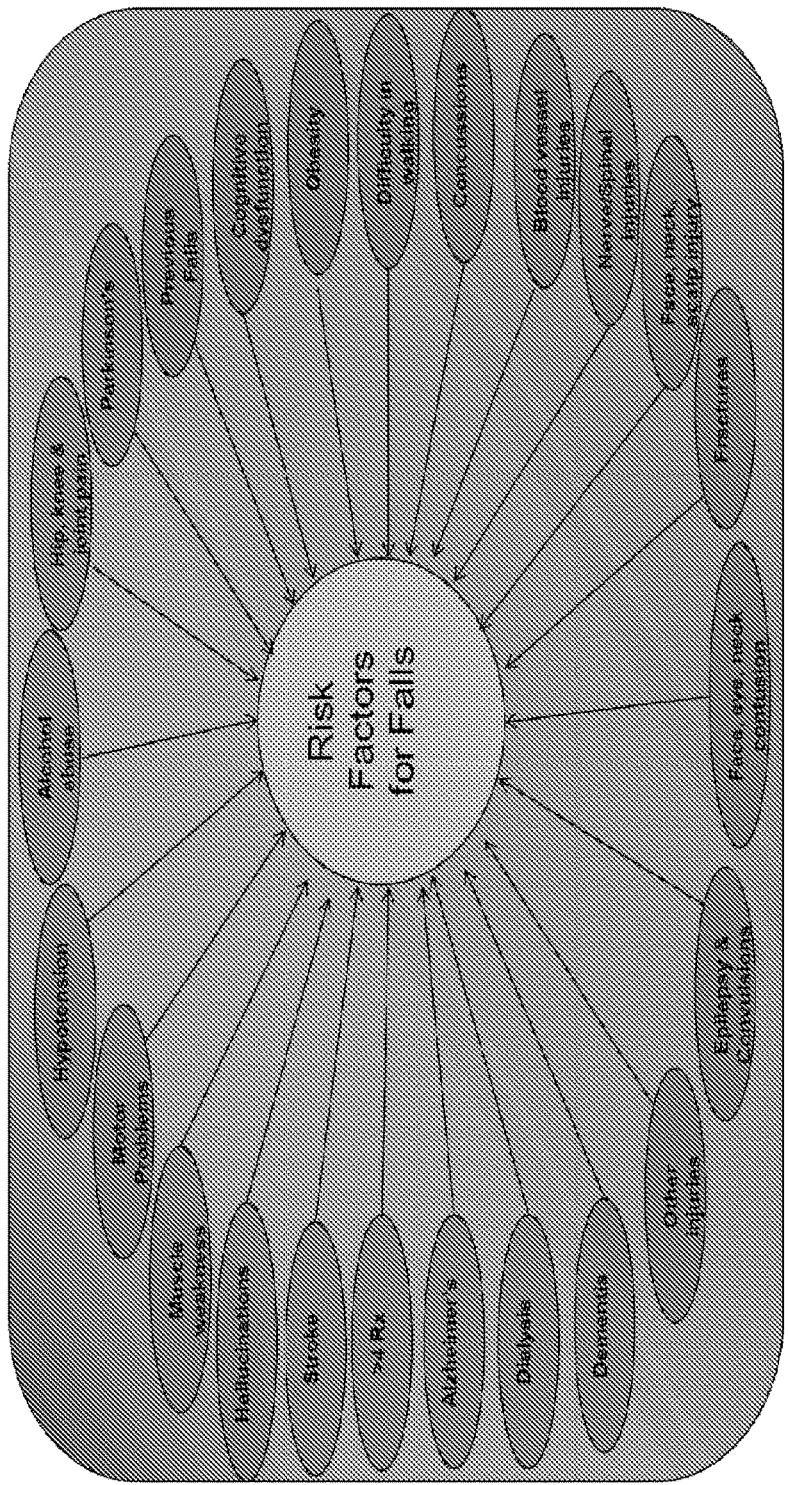
FIG. 3 is a diagram of triggers or risk factors considered relevant to a risk population of falls according to an example embodiment.

In the example shown, 1.7 million cases (1,770,610) were considered for building the predictive model. The data consisted of members enrolled in plans from 2009 to 2010. For the disclosed example, these members had claims related to one of the twenty-four different medical conditions listed in FIG. 3. A random sample of 40% of the data was used to train the model, 10% was used to validate the model, and the remaining 50% was used as the test data set. About 357,929 of the cases had at least once incidence of a fall in 12 months after the score date giving a target prevalence of about 20%. Because falls are often underreported in the claims data, a definition of falls based on a plurality of medical conditions may be used to implement the disclosed computer-implemented system and method. For example, different conditions such as unintentional falls, skull fractures, neck and trunk fracture, upper limb fracture, lower limb fracture, and dislocation may be used as a proxy for falls from claims data. The presence of these conditions in member claims and other data served as indicators regarding the likelihood of a fall occurring within a specified period. While the disclosed system and method use these six conditions as a proxy for falls, other conditions may be substituted for the disclosed conditions or additional conditions may be considered.

Figure 4:
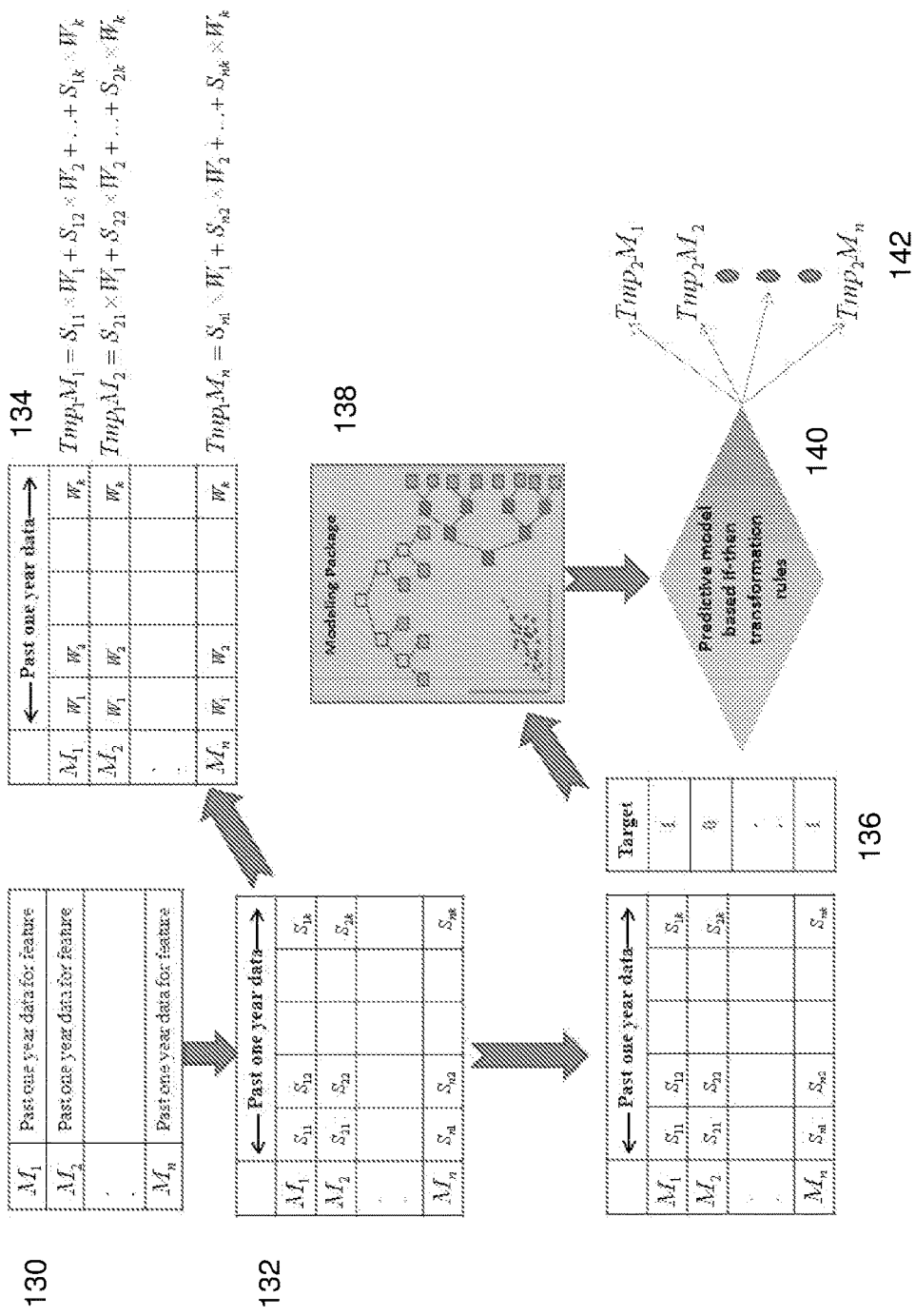
FIG. 4 is a diagram of temporal feature extraction from existing medical features.

Referring to FIG. 4, a diagram of temporal feature extraction from an existing feature set is shown. Two different types of temporal feature extraction strategies are explained. In an example embodiment, the historical one year data 130 is divided into k non-overlapping periods 132. Instead of aggregating the feature value for entire one year, the features are aggregated based on these k periods ($S_1, S_2, \ldots S_k$). For example, claims may be aggregated for each month or each quarter of the year. In one strategy, weights are assigned to each of these segments $w_1, w_2, \ldots w_k$ 134. The temporal feature ($Tmp_1$) is then calculated by aggregating the product of feature value in each segment with the segment weight $Tmp_1 = S_1 \times w_1 + S_2 \times w_2 + \ldots + S_k \times w_k$ 134. In yet another strategy, target (Falls/No-falls) 136 is added to the segmented dataset 138 and a predictive model 140 is fit to this dataset. Rules are then extracted from the fitted model to transform existing feature into its temporal version ($Tmp_2$) 142.

Figure 5:
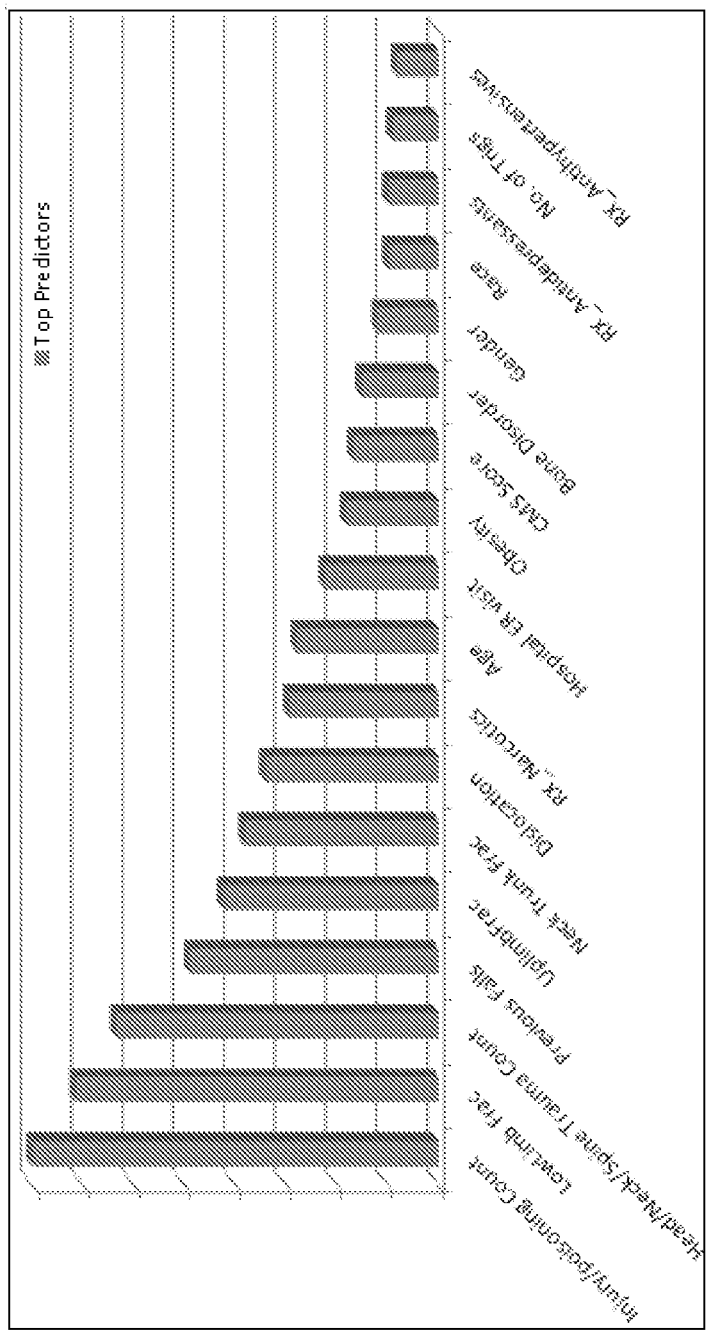
FIG. 5 is a diagram of top predictors that help identify the risk for falls according to an example embodiment.

Referring to FIG. 5, a diagram of variables considered and associated importance of falls according to an example embodiment is shown. Some of the top predictors were identified and details of the numbers associated with the top predictors are shown in the Tables 3, 4, 5, 6 and 7. The importance (Chi Square value for category variables and correlation value for continuous variables) is a statistical measure to examine the relationship between the individual variable and the dependent variable. The higher value represents more significant relationship.

Top Risk Factors and Some Explanation

TABLE 3

Falls Rate by Age Group

| Age | Fall Rate |
| --- | --- |
| <25 | 15.77% |
| 26 to 35 | 17.86% |
| 36 to 45 | 19.22% |
| 46 to 55 | 19.71% |
| 56 to 65 | 18.74% |
| 66 to 75 | 16.57% |
| 76 to 85 | 22.09% |
| >85 | 31.48% |
| Total | 20.21% |

TABLE 4

Falls Rate by Gender

| Gender | Fall Rate |
| --- | --- |
| Female | 21.76% |
| Male | 17.29% |
| Total | 20.21% |

TABLE 5

Falls Rate by CMS Risk Score

| CMS | Fall Rate |
| --- | --- |
| <=0.5 | 15.61% |
| 0.5 to 1.0 | 17.23% |
| 1.0 to 3.0 | 23.17% |
| 3.0 to 5.0 | 30.09% |
| 5.0 to 8.0 | 34.62% |
| 8.0 to 10.0 | 27.49% |
| >10.0 | 30.04% |
| Total | 20.21% |

TABLE 6

Falls Rate by Previous Falls

| Claim Count | Fall Rate |
| --- | --- |
| 0 | 17.40 |
| 1 | 41.88 |
| 2 | 47.05 |
| 3 | 53.17 |
| >3 | 59.49 |
| Total | 20.21% |

TABLE 7

Falls Rate by Different Medications

| Claim Count | Fall Rate |
|---|---|
| Narcotics | |
| 0 | 15.98 |
| 1 | 20.65 |
| 2 | 24.34 |
| >2 | 27.31 |
| Chronic Meds | |
| 0 | 22.37 |
| 1 | 17.90 |
| 2 | 16.75 |
| >2 | 20.37 |
| Antidepressants | |
| 0 | 18.03 |
| 1 | 22.72 |
| 2 | 24.26 |
| >2 | 25.10 |
| Antihypertensives | |
| 0 | 20.84 |
| 1 | 19.76 |
| 2 | 20.04 |
| >2 | 18.28 |

Figure 6:
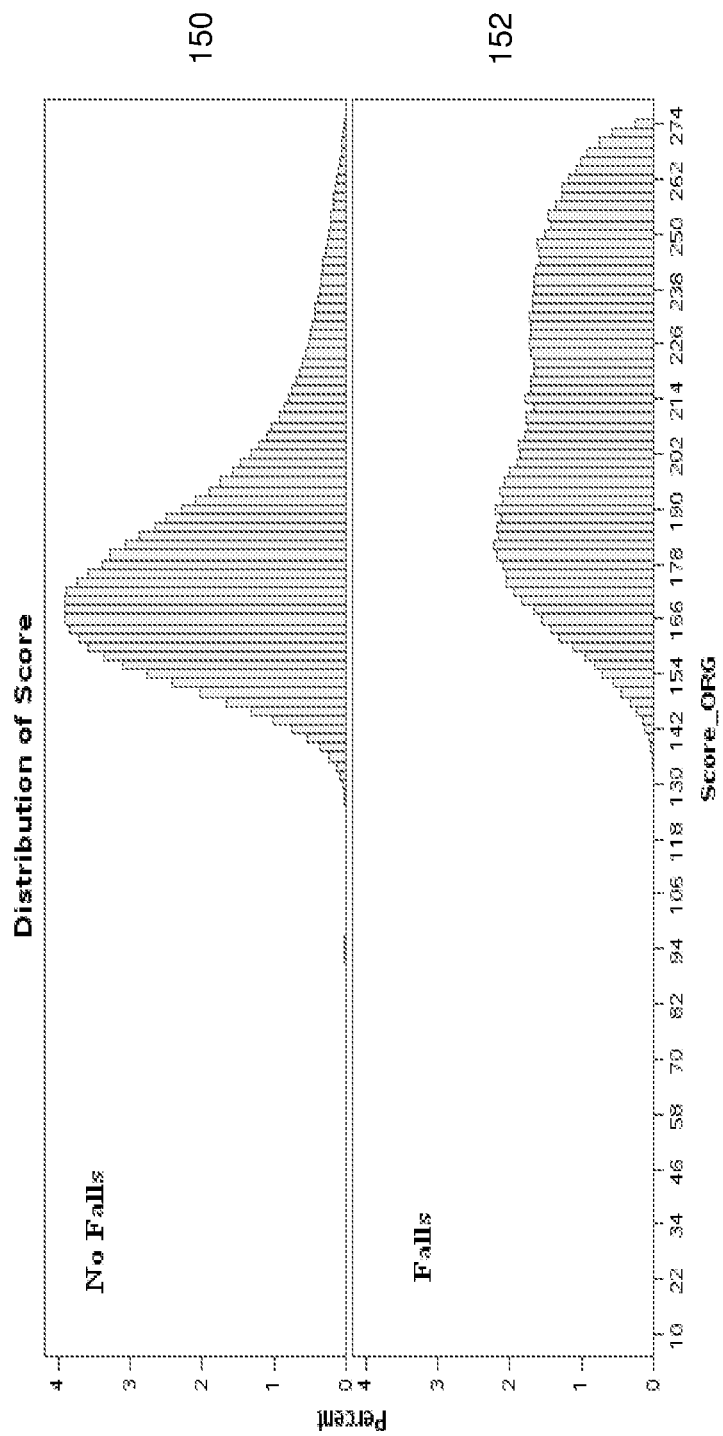
FIG. 6 is a score distribution comparison for members that do not and do have a fall according to an example embodiment.

Referring to FIG. 6, a score distribution comparison for members who had a fall 150 and those who did not have any fall 12 months after being identified at risk of fall 152 according to an example embodiment is shown. As can be seen from the two score distributions in FIG. 6, the population with a fall within 12 months after score date 152 has higher risk score compared with the risk score for the population without any falls 150 in the 12 months after scoring. Details of the numbers associated with the risk scores are shown in the Table 8. The mean for the population with at least one fall is significantly higher at 208.82 compared to the mean of population with no fall at 179.27.

TABLE 8

Statistics for the risk scores (Test set only)

| Event | Mean | Std Dev | Minimum | Maximum |
|---|---|---|---|---|
| No Fall | 179.2765 | 24.9701 | 9.5465 | 274.9344 |
| Having Fall | 208.8207 | 32.4518 | 89.0164 | 275.3222 |

Figure 7:
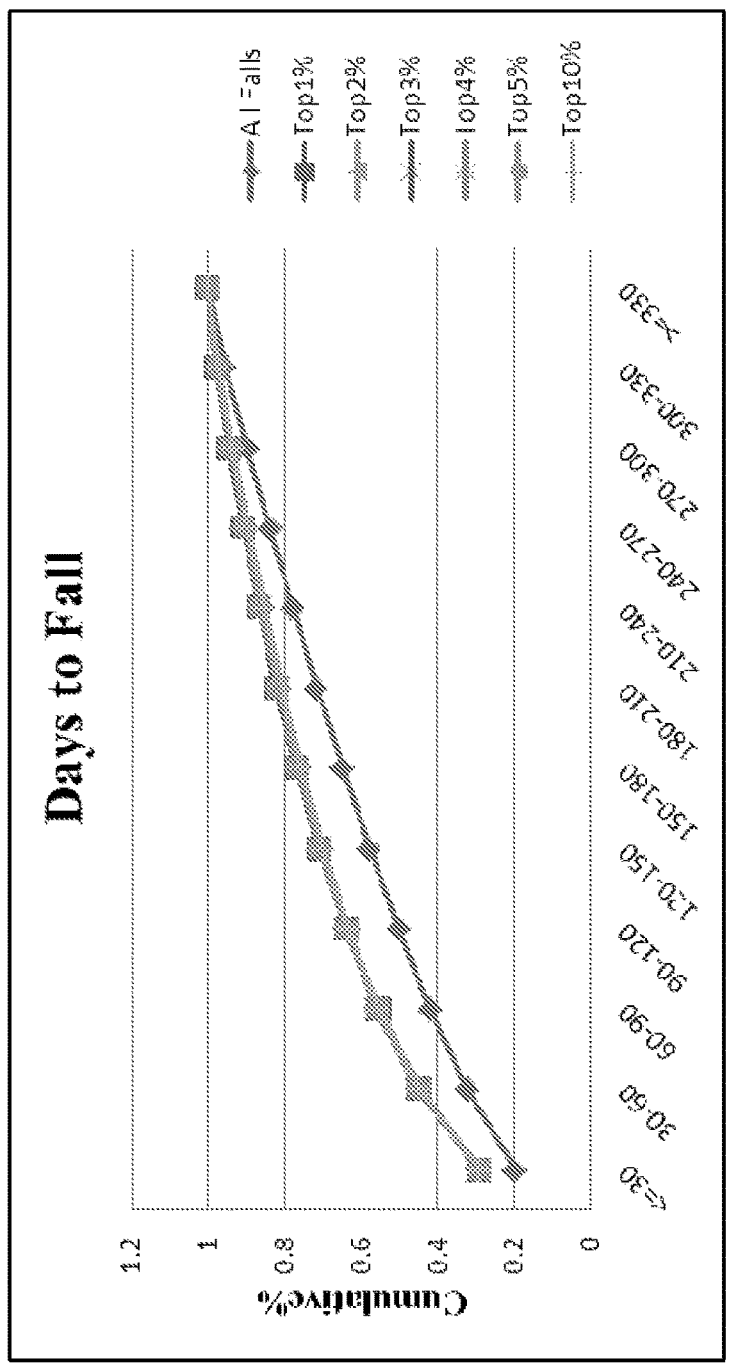
FIG. 7 a diagram of the distribution of days to fall according to an example embodiment.

Referring to FIG. 7, a diagram of the distribution of days to event according to an example embodiment is shown. The falls predictive model selects a group of people who have been identified at risk of falling based on one of the 24 triggers. Falls model generates a score for every member in this list. Based upon the score, a member is placed into an intervention program tailored to assist them. As seen in the example, the distribution of days to event are compared for different risk groups including the top 1%, top 2%, top 3%, top 4%, top 5%, top 10%, and all members (overall). Members are scored and then sorted from the highest risk score to the lowest risk score. Members in top 1% group represent the highest at risk 1% members. A closer look at the distribution of days show that the days to fall after score date is very similar for all groups. This result shows there is equal opportunity for helping members in different risk groups although the type of intervention programs for each group could be different.

The disclosed predictive model software application may be accessible through an online server and receive data from a clinical profile database in response to a trigger. A trigger (one of the 24 risk factors) may be used to invoke the falls predictive model and to calculate the risk score of a member based on a change in the member's profile or clinical data. After a score is calculated, the falls probability/score for a member may be used to drive a clinical care system used by nurses/clinical specialists to access the member's clinical profile and claims data. The model can provide information about significant predictors for individual members which may be highly correlated to the event. Nurses/clinical specialists can then assist patients in providing the right type of intervention.

Because members fall into various risk groups; top 1%, top 2%, etc.; different risk stratification strategies can be developed based on risk score range. Table 9 shows some details about the different score ranges. Various transformation techniques may be applied to change a probability to a more user-friendly numeric score. As illustrated in the table, the overall rate of falls is 20%, but the rate of fall in the top 1% group is almost three times that rate at 76%. This information is very important when resources and time are limited. For example, 100,000 members may be at risk but only 1% (or 1000) members can be selected for an intervention. If random selection is performed to identify 1000 members, only 200 of those at risk of falling may be impacted. However, if model scoring is applied to identify the top 1% high risk members, 760 members are impacted. Use of the model results in assistance for an additional 560 members.

TABLE 9

Risk Stratification

| Population | % Expected to have a Fall in the next 12 Months after score date | Score Range |
|---|---|---|
| Top 1% | 76.17% | >=264 |
| Top 2% | 73.10% | >=258 |
| Top 5% | 67.05% | >=245 |
| Top 10% | 60.03% | >=230 |
| Top 20% | 49.24% | >=207 |
| Top 50% | 31.79% | >=178 |

Specialized Emergency Room (ER) Falls Model

In another example embodiment, the falls model is used to predict falls leading to ER visits. The model uses similar triggers as previously described in the falls prediction model but predicts a risk of fall leading to ER visit by the patient. The output of the predictive model is a risk score that indicates the likelihood of having a fall resulting in an ER visit. In the example shown, 1.7 million cases (same as fall model described previously) were considered for building the predictive model. The data consisted of members enrolled in plans from 2009 to 2010. These members had claims related to one of the twenty-four different medical conditions listed in FIG. 3. A random sample of 40% of the data was used to train the model, 10% was used to validate the model, and the remaining 50% was used as the test data set. About 51,645 of the cases had at least once incidence of fall in 12 months after the score date giving a target prevalence of about 3.01%. As is evident from the statistics the percentage of members with this very specific target, fall resulting in ER visit, is very small compared to all case falls. This result makes the prediction harder. The model building strategy is similar to the previously described falls prediction model except the target population is different. This results in a very specific ER falls prediction model.

Figure 8:
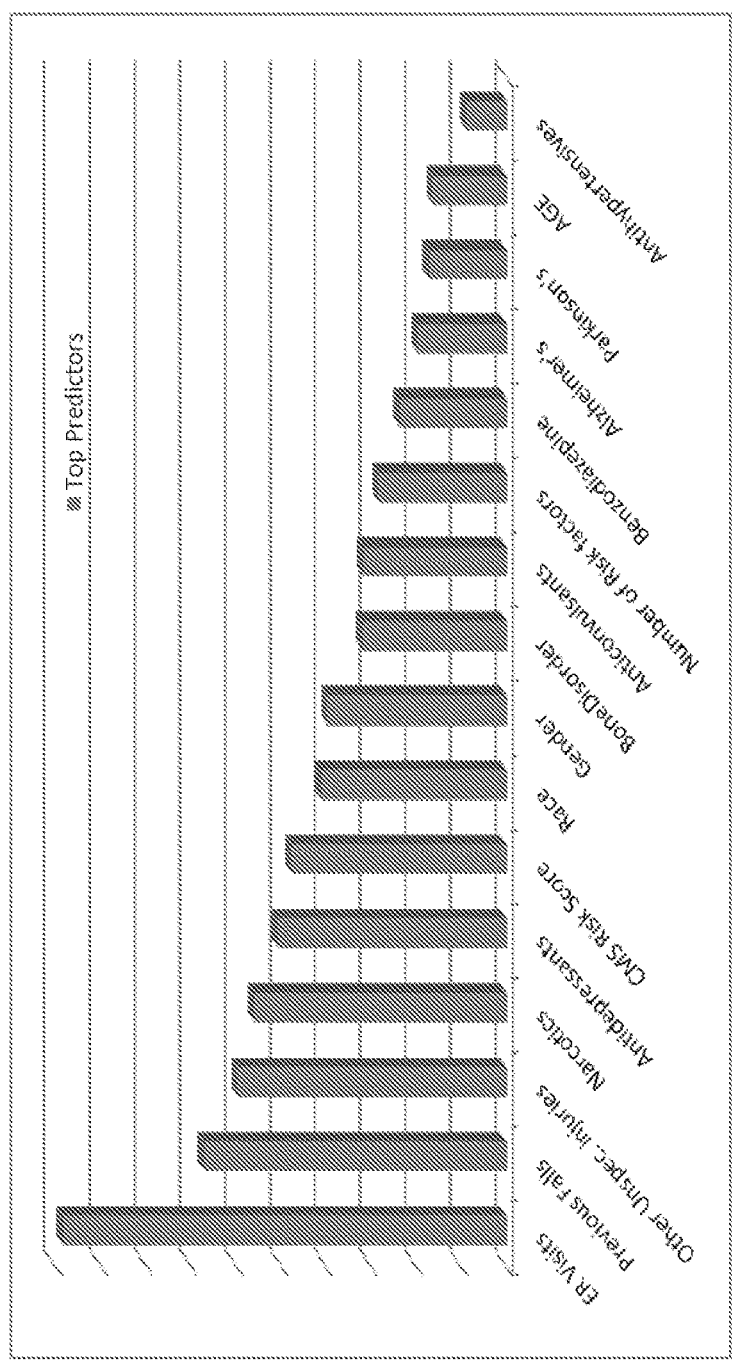
FIG. 8 is a diagram of top predictors that help identify the risk for falls resulting in emergency room visits according to an example embodiment.

Referring to FIG. 8, a diagram of variables considered and associated importance of ER falls according to an example embodiment are shown. Because both the falls model and the ER falls model use the same trigger population and same predictors, it is expected to see the same predictors appear in the top predictors list for both models. However, the order/importance of these predictors varies depending upon the model. For example, ER visits are the top predictor for ER falls but not as important for falls while injury/poisoning count is important for falls but not equally important for ER falls. An ER falls model may be used to augment an ER strategy, which may be very different from other intervention strategies.

Just as in the falls model, members may be segmented into various risk groups: top 1%, top 2%, etc. Different risk stratification strategies can be developed based on risk score range. Table 10 shows some details about the different score ranges. As illustrated, the overall rate of falls resulting in ER visits is 3%, but the rate of fall in the top 1% group is almost six times that at 18%.

TABLE 10

Risk Stratification for ER Falls Prediction model

| Population | % Expected to have a Fall in the next 12 Months after score date | Score Range |
|---|---|---|
| Top 1% | 18.86% | >=184 |
| Top 2% | 15.29% | >=174 |
| Top 5% | 11.63% | >=156 |
| Top 10% | 9.02% | >=148 |
| Top 20% | 7.12% | >=129 |
| Top 50% | 4.67% | >=114 |
| Whole risk population | 3.01% | >=2 |

While certain embodiments of the present invention are described in detail above, the scope of the invention is not to be considered limited by such disclosure, and modifications are possible without departing from the spirit of the invention as evidenced by the data. One skilled in the art would recognize that such modifications are possible without departing from the scope of the claimed invention.

APPENDIX A

Temporal Feature Extraction Strategies

This appendix summarizes some Temporal feature extraction strategies from the medical claim features. Because medical claims data is gathered over a period of time these strategies may be used to transform raw features into temporal features. Ideally, feature value changes over time such as number of claims, charged amount, number of hospital admissions etc.

Strategy 1: In this strategy, a numerical score per feature is calculated. The strategy can be applied to both aggregate type features where each claim value differs (e.g., Amount of Money paid out) or the count type features where each claim has a value of 1 or 0 (e.g., Back Claim=1 for Yes and 0 for No, or Radiology Claim=1 for Yes and 0 for No). This strategy produces a continuous valued temporal feature.

Figure 9:
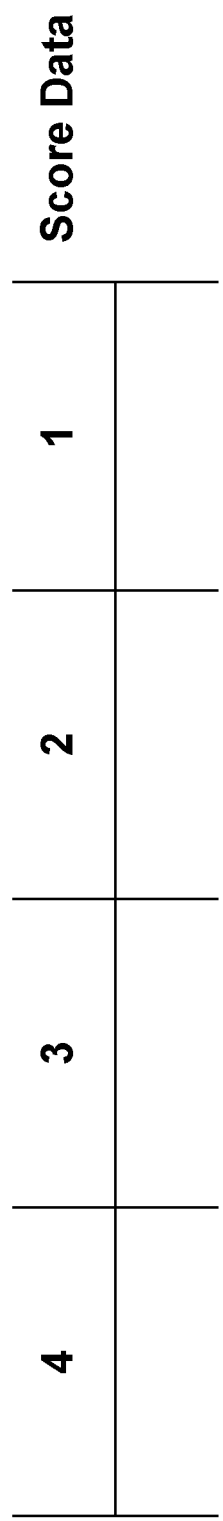
FIG. 9 is an exemplary score data chart.

Step-by-Step Methodology:
1. For each feature gather data for the past 1 year from the score date.
2. Divide this complete data range into four intervals/quarters where each interval represents data for 3 months (4×3=12 Months=1 Year), such as in the chart shown in FIG. 9.
3. Label each interval from 1-4 with the interval closest to the Score date getting a label of 1 and the interval farthest from score date getting a label of 4.
4. For individual features do the following:
   a. If the current feature being analyzed is of type Aggregate, then get a total sum of all the aggregates in each interval
      Example:— Assuming 5 claims in $1^{st}$ interval of amount 30, 20, 25, 40, and 45 respectively, 3 claims in $2^{nd}$ interval of amount 25, 30, and 20 respectively, 2 claims in $3^{rd}$ interval of amount 20 and 40 respectively, and 1 claim in $4^{th}$ interval of amount 25. Then the total sums for each interval are as follows:
      Interval 1=30+20+25+40+45=160;
      Interval 2=25+30+20=75;
      Interval 3=20+40=60;
      Interval 4=25
   b. If the current feature being analyzed is of type Count, then simply get the number of counts in each interval.
      Example:— Assuming there are 5 claims in $1^{st}$ interval of amount 30, 20, 25, 40, and 45 respectively, 3 claims in $2^{nd}$ interval of amount 25, 30, and 20 respectively, 2 claims in $3^{rd}$ interval of amount 20 and 40 respectively, and 1 claim in $4^{th}$ interval of amount 25. Then the total sums for each interval are as follows:
      Interval 1=5;
      Interval 2=3;
      Interval 3=2;
      Interval 4=1
5. Assign weights to each of the four intervals in a decreasing fashion such that the interval closest to score date gets the highest weight and the interval farthest from the score date gets the lowest weight. For example, a weight of 1 for interval 1, ½ for interval 2, ⅓ for interval 3, and ¼ for interval 4.
6. Multiply these weights with the respective Sum/Count in each interval. This gives a weighted Sum/Count for each interval.
Example:—
Type Aggregate: Interval 1=160*1, Interval 2=75*½, Interval 3=60*⅓, and Interval 4=24*¼.
Type Count: Interval 1=5*1, Interval 2=3*½, Interval 3=2*⅓, and Interval 4=1*¼
7. Add the weighted Sum/Count from all the intervals to get a cumulative Sum.
Example:—
Type Aggregate: (160*1)+(75*½)+(60*⅓)+(24*¼)=160+37.5+20+6=223.5
Type Count: (5*1)+(3*½)+(2*⅓)+(1*¼)=5+1.5+0.666+0.25=7.416
8. This cumulative sum (223.5 for Aggregate and 7.416 for Count) now represents the temporal feature value.

The output of this strategy is a continuous numerical value. People with most claims closer to a score date will get a higher score compared to people with most claims farther from score date.

Strategy 2: In this strategy both the magnitude (i.e. the amount/count) and the pattern are taken into account to generate a temporal trend. The strategy can again be applied to both Aggregate type features where each claim value differs (e.g., Amount of Money paid out) or the Count type features where each claim has a value of 1 or 0 (e.g., Back Claim=1 for Yes and 0 for No, or Radiology Claim=1 for Yes and 0 for No). For each quarter, find the magnitude labeled "high, low, and normal" based on the mean of the values in that quarter. The quarters are then transformed into individual features each having a value of high, low or normal. A decision tree is built using only these four features and the Target to get branches leading to a target decision. These branches then become the new patterns which can be labeled and used as a feature value for a single categorical temporal feature. Step-by-Step methodology:

1. For each feature gather data for the past 1 year from the score date.
2. Divide this complete data range into 4 intervals/quarters where each interval represents data for 3 months (4×3=12 Months=1 Year), such as in the chart shown in FIG. 9.
3. Label each interval from 1-4 with the interval closest to the Score date getting a label of 1 and the interval farthest from score date getting a label of 4.
4. For individual features:
   a. If the current feature being analyzed is of type Aggregate, then get a total sum of all the aggregates in each interval
   Example (From Strategy 1):—
   Interval 1=30+20+25+40+45=160;
   Interval 2=25+30+20=75;
   Interval 3=20+40=60;
   Interval 4=25
   b. If the current feature being analyzed is of type Count, then get the number of counts in each interval.
   Example (From Strategy 1):—
   Interval 1=5;
   Interval 2=3;
   Interval 3=2;
   Interval 4=1
5. Find the average for each interval over the complete population.
6. Label each interval for the current transaction as high, low, or normal as follows:
   If $-0.10*\overline{X}_i \leq V_i - \overline{X}_i \leq 0.10*\overline{X}_i$, where $\overline{X}_i$=mean of the Interval i, and $V_i$=current value of Interval i, then label normal.
   If $V_i - \overline{X}_i < -0.10*\overline{X}_i$, then label low
   Else label high.
7. Create a new Dataset by using these individual as features so that one feature represents one interval and the value of the feature represents the value of an interval for a particular transaction/claim. This gives a dataset with 4 variables.

| | |
|---|---|
| Person 1 | Interval1 Cnt = 5 |
| | Interval2 Cnt = 3 |
| | Interval3 Cnt = 2 |
| | Interval4 Cnt = 1 |
| Person 2 | Interval1 Cnt = 7 |
| | Interval2 Cnt = 9 |
| | Interval3 Cnt = 4 |
| | Interval4 Cnt = 8 |
| Person | Interval1 Cnt = . . . |
| | . . . |
| | . . . |
| | . . . |
| | . . . |

| P. No. | Interval 1 Cnt | Interval 2 Cnt | Interval 3 Cnt | Interval 4 Cnt | Target |
|---|---|---|---|---|---|
| Person 1 | High | Normal | Low | Low | 1 |
| Person 2 | High | High | Normal | High | 0 |
| . . . | | | | | |
| Person n | | | | | |

8. Add the binary target variable as the $5^{th}$ variable to this new dataset.
9. Fit a decision tree to this new dataset.
10. The branches of the decision trees leading to a decision form the new temporal patterns.
Use the predicted probability as the new temporal feature value Since the output of this strategy is a numeric probability, it can be used as a categorical label or a continuous numeric value. This strategy is a modification of the methodology from [5].

REFERENCES

[1] http://www.cdc.gov/HomeandRecreationalSafety/Falls/adultfalls.html.
[2] Emergency Department Visits for Injurious Falls among the Elderly, AHRQ Statistical Brief #80, 2006.
[3] Risk Factors associated with hospitalization for unintentional falls: Wisconsin hospital discharge data for patients aged 65 and over, Wisconsin Medical Journal, 2003, Vol. 102, No. 4.
[4] Medications and Falls in the Elderly: A Review of the evidence and practical considerations, Pharm. Therapy P&T Journal, November 2003, Vol. 28, No. 11.
[5] Verduijn M., Sacchi L., Peek N., Bellazzi R., Jonge E. D., Mol B. A. J. M. D., "Temporal Abstraction for feature extraction: A comparative case study in prediction from intensive care monitoring," *Elsevier Artificial Intelligence in Medicine*, Vol. 41, Issue 1; 2007; pp. 1-12.
[6] Chung P. V., Anh D. T., "Applying Temporal Abstraction in Clinical Databases," *IEEE International Conference Research, Innovation, and Vision of the Future*; March 2007; pp. 192-199.
[7] Kahn M. G., Fagan L. M., Sheiner L. B., "Model-Based Interpretation of Time-Varying Medical Data," *Proceedings of Annual Symposium of Computer Applications in Medical Care*; November 1989; pp. 28-32.

What is claimed is:
1. A computer-implemented system for identifying a member of a health insurance market-based member population at risk for falling within a predetermined time period, the system comprising:
   (a) one or more computing devices storing:
      (1) falls model triggers comprising
         alcohol abuse, Alzheimer's disease, blood vessel injury, cognitive dysfunction, concussion, dementia, dialysis, difficulty walking, epilepsy and convulsion, face, eye, or neck contusion, face, neck, or scalp injury, fracture, hallucinations, hip, knee or joint pain, hypotension, motor problems, muscle weakness, nerve or spinal injury, obesity, one or more previous falls, other injury, Parkinson's disease, and stroke;
      (2) falls predictors comprising injury/poisoning incidence count, a lower limb fracture, head, neck, or spine trauma incidence count, previous falls, an upper limb fracture, a neck or trunk fracture, a dislocation, a narcotic prescription, age, a hospital emergency room visit, obesity, governmental agency health score, a bone disorder, gender, race, an anti-depressant prescription, and an anti-hypertensive prescription; and (b) one or more computing devices executing instructions to:

(1) receive member data and consumer data for the entire health insurance market-based member population, wherein said member data comprises data selected from the group consisting of: medical claims data and pharmacy claims data, wherein said consumer data comprises data selected from the group consisting of:
demographic data, geographic data, and financial data;

(2) analyze said received member data for the entire health insurance market-based member population to identify a subset of members within said health insurance market-based member population having one or more of said falls model triggers present in said member's data;

(3) process the member data and said consumer data for said subset of members using an algorithm selected from the group consisting of: variable selection, principle component analysis, and clustering;

(4) extract features from the member data for said subset of members by temporal feature extraction, wherein said falls predictors are selected to correspond with the extracted features;

(5) provide a plurality of training conditions to a computing device that comprises a falls predictive model, said training conditions comprising an unintentional fall, a skull fracture, a neck fracture, a trunk fracture, an upper limb fracture, a lower limb fracture, and a dislocation of bones;

(6) develop the falls predictive model using a modeling technique selected from the group consisting of: decision tree, logistic regression, artificial neural networks, and ensemble;

(7) provide said member data and said consumer data for said subset of members to the computing device that comprises said falls predictive model;

(8) receive a calculated falls risk score from the computing device that comprises said falls predictive model, wherein said falls risk score represents the likelihood that the respective member of said subset of members will visit an emergency room as a result of experiencing a fall within the predetermined time period, and wherein said calculated falls risk score is determined at least in part based on the presence or absence of each of said falls predictors in said member data for the respective member;

(9) sort the received calculated falls risk score into one of a plurality of groups according to a severity level indicated by the received calculated falls risk score;

(10) assign a clinical program or intervention for each of the members in said subset of members, wherein said assignment is determined based on the group into which said member's calculated falls risk score has been sorted, where said intervention is adapted to reduce the member's calculated falls risk score; and

(11) enroll said member in said assigned clinical program or intervention.

2. The computer-implemented system of claim 1 wherein the temporal feature extraction is accomplished by executing software instructions which cause the one or more computing devices to:

gather member data for each feature for a time period prior to a date in question, wherein said member data comprises a number of events, each of which is associated with a particular time;

divide the time period into a number of equal intervals spanning the time period;

sort the gathered data such that each event is sorted into the interval corresponding with the particular time for the respective event;

sum the data falling within each interval;

assign a weighting to each interval in decreasing fashion such that the interval temporally closest to the date in question gets the highest weight and the interval temporally farthest from the date in question gets the lowest weight;

multiply the summed value for each interval by the weighting for the respective interval to determine a weighted sum for each interval; and sum the weighted sums to determine a cumulative sum, wherein the cumulative sum is utilized to determine the calculated falls risk score.

3. The computer-implemented system of claim 1 wherein the temporal feature extraction is accomplished by executing software instructions which cause the one or more computing devices to:

gather member data for each feature for a time period prior to a date in question, wherein said member data comprises a number of events, each of which is associated with a particular time;

divide the time period into a number of equal intervals spanning the time period;

sort the gathered data such that each event is sorted into the interval corresponding with the particular time for the respective event;

fit a predictive model to determine a temporal feature value for each extracted feature; and weight each extracted feature with the respective temporal feature value, wherein the weighted values are utilized to determine the calculated falls risk score.

* * * * *